(12) United States Patent
Sasao et al.

(10) Patent No.: US 8,088,177 B2
(45) Date of Patent: Jan. 3, 2012

(54) HAIR COSMETIC COMPOSITION

(75) Inventors: Yuki Sasao, Aichi-ken (JP); Yasue Yamazaki, Aichi-ken (JP)

(73) Assignee: Hoyu Co., Ltd., Aichi-Ken (JP)

( * ) Notice: Subject to any disclaimer, the term of this patent is extended or adjusted under 35 U.S.C. 154(b) by 0 days.

(21) Appl. No.: 13/131,437

(22) PCT Filed: May 28, 2010

(86) PCT No.: PCT/JP2010/059078
§ 371 (c)(1),
(2), (4) Date: May 26, 2011

(87) PCT Pub. No.: WO2010/140542
PCT Pub. Date: Dec. 9, 2010

(65) Prior Publication Data
US 2011/0236328 A1 Sep. 29, 2011

(30) Foreign Application Priority Data
Jun. 1, 2009 (JP) .................................. 2009-132586

(51) Int. Cl.
*A61Q 5/10* (2006.01)

(52) U.S. Cl. .............. 8/405; 8/431; 8/435; 8/552; 8/580
(58) Field of Classification Search .............. 8/405, 431, 8/435, 552, 580
See application file for complete search history.

(56) References Cited

U.S. PATENT DOCUMENTS 6,036,730 A * 3/2000 Yoshida et al. ................... 8/406

FOREIGN PATENT DOCUMENTS

| | | | |
|---|---|---|---|
| JP | 05-221840 | A | 8/1993 |
| JP | 08-217650 | A | 8/1996 |
| JP | 08-268848 | A | 10/1996 |
| JP | 11-152215 | A | 6/1999 |
| JP | 2004-175748 | A | 6/2004 |
| JP | 2008-100922 | A | 5/2008 |
| WO | 2008/096497 | A1 | 8/2008 |

* cited by examiner

*Primary Examiner* — Eisa Elhilo
(74) *Attorney, Agent, or Firm* — Seager, Tufte & Wickhem LLC

(57) ABSTRACT

A hair cosmetic composition used for dyeing, bleaching, or destaining hair contains diglycerin, 1,3-butylene glycol, and polyethylene glycol having a number average molecular weight of 10,000 or more.

3 Claims, No Drawings

HAIR COSMETIC COMPOSITION

TECHNICAL FIELD

The present invention relates to a hair cosmetic composition used for dyeing, bleaching, or destaining hair.

BACKGROUND ART

Generally, a hair cosmetic composition used for dyeing, bleaching, or destaining hair contains an alkaline agent and an oxidizing agent. The oxidizing agent acts to remove melanin from hair. The alkaline agent acts to improve lightness of bleached hair by promoting the action of the oxidizing agent. When a hair cosmetic composition contains a dye, the alkaline agent also acts to improve the dyeability of hair by swelling hair so as to improve the permeability of the dye into the hair. A surfactant, an oil component, or a polymer may be added to a hair cosmetic composition. In that case, a certain viscosity is imparted to the hair cosmetic composition, by which dripping is prevented and the adherability of the composition to hair is improved. An organic solvent may be added to a hair cosmetic composition in order to improve the spreadability of the composition.

Patent Document 1 discloses a hair cosmetic composition used for bleaching or dyeing hair containing amino-modified silicone, highly polymerized silicone, and a cationic polymer. Patent Document 1 discloses that the composition may further contain ethanol, which is an organic solvent (for example, refer to Table 2).

PRIOR ART DOCUMENTS

Patent Document 1: Japanese Laid-Open Patent Publication No. 2004-175748

SUMMARY OF INVENTION

Technical Problems to be Solved by the Invention

However, a problem has been that the hair cosmetic composition disclosed in Patent Document 1 quickly dries after being applied to hair, and the viscosity of the composition is increased with time. Particularly, when hair is combed after a certain period of time after application of the hair cosmetic composition, it is difficult to spread the composition over the entire hair, and for this, in some cases hair is not evenly bleached or dyed.

The present inventors have conducted intensive research. As a result, they have found that the aforementioned problem can be solved by using specific multiple polyhydric alcohols in combination, based on which the present invention was completed. An objective of the present invention is to improve the ease of application of a hair cosmetic composition used for dyeing, bleaching, or destaining hair to hair so that hair can be evenly dyed, bleached, or destained with the hair cosmetic composition.

Means for Solving the Problems

In order to achieve the aforementioned objective, and in accordance with one aspect of the present invention, a hair cosmetic composition used for dyeing, bleaching, or destaining hair is provided that contains diglycerin, 1,3-butylene glycol, and polyethylene glycol having a number average molecular weight of 10,000 or more.

The number average molecular weight of polyethylene glycol used is preferably 20,000 or more.

Preferably, the hair cosmetic composition contains 0.005 to 10% by mass, 0.05 to 15% by mass, and 0.0005 to 5% by mass of the aforementioned diglycerin, 1,3-butylene glycol, and polyethylene glycol, respectively.

Effects of the Invention

According to the present invention, the ease of application of a hair cosmetic composition used for dyeing, bleaching, or destaining hair to hair is improved, and hair can be evenly dyed, bleached, or destained with the hair cosmetic composition.

MODE FOR CARRYING OUT THE INVENTION

First Embodiment

Hereinbelow, a first embodiment, in which the present invention is embodied as a first, a second, and a third cosmetic composition used for bleaching or destaining hair, will be described.

(First Hair Cosmetic Composition)

The first hair cosmetic composition is a two-part type composed of a first and a second agent, which are mixed upon application, used for bleaching or destaining hair. The first agent contains diglycerin, 1,3-butylene glycol, polyethylene glycol, and an alkaline agent. The second agent contains an oxidizing agent.

(First Agent of First Hair Cosmetic Composition)

Diglycerin, 1,3-butylene glycol, and polyethylene glycol contained in the first agent each act to improve the ease of application of the first hair cosmetic composition to hair when used in combination, which enables uniform bleaching or destaining of hair by the first hair cosmetic composition.

The diglycerin content in a mixture of the first and second agents is preferably 0.005 to 10% by mass, more preferably 0.05 to 5% by mass, and further preferably 0.25 to 2.5% by mass. When the diglycerin content is somewhere within the aforementioned ranges, the uniformity of bleaching or destaining of hair by the first hair cosmetic composition is improved. Particularly, when the diglycerin content is 10% by mass or less, the ease of application of the first hair cosmetic composition to hair is improved, by which it becomes easy to realize the uniformity of bleaching or destaining of hair by the first hair cosmetic composition.

The 1,3-butylene glycol content in a mixture of the first and second agents is preferably 0.05 to 15% by mass, more preferably 0.5 to 10% by mass, and further preferably 1.5 to 5% by mass. When the 1,3-butylene glycol content is somewhere within the aforementioned ranges, the uniformity of bleaching or destaining of hair by the first hair cosmetic composition is improved. Particularly, when the 1,3-butylene glycol content is 0.05% by mass or more, drying of the first hair cosmetic composition applied on hair is delayed, by which the ease of application of the first hair cosmetic composition to hair is improved. For this, it becomes easy to realize the uniformity of bleaching or destaining of hair by the first hair cosmetic composition.

The number average molecular weight of polyethylene glycol used must be 10,000 or more, and is preferably 20,000 or more, and more preferably 30,000 or more. When polyethylene glycol having a number average molecular weight of less than 10,000 is used, the uniformity of bleaching or destaining of hair by the first hair cosmetic composition is impaired. The upper limit of the number average molecular weight of polyethylene glycol used is preferably 5,000,000, although no particular limitation is imposed thereon. When polyethylene glycol having a number average molecular weight of 5,000,000 or less is used, the production cost of the first hair cosmetic composition is kept low.

The polyethylene glycol content in a mixture of the first and second agents is preferably 0.0005 to 5% by mass, more preferably 0.005 to 2.5% by mass, and further preferably 0.025 to 1% by mass. When the polyethylene glycol content is somewhere within the aforementioned ranges, the uniformity of bleaching or destaining of hair by the first hair cosmetic composition is improved. Particularly, when the polyethylene glycol content is 5% by mass or less, the ease of application of the first hair cosmetic composition to hair is improved, by which it becomes easy to realize the uniformity of bleaching or destaining of hair by the first hair cosmetic composition.

An alkaline agent contained in the first agent acts to bleach or destain hair by promoting the action of an oxidizing agent contained in the second agent. Examples of the alkaline agent used include ammonia, alkanolamine, organic amine, inorganic alkali, a basic amino acid, and a salt of these substances. Specific examples of the alkanolamine include monoethanolamine and triethanolamine. Specific examples of the organic amine include 2-amino-2-methyl-1-propanol (AMP), 2-amino-2-methyl-1,3-propanediol, and guanidine. Specific examples of the inorganic alkali include sodium hydroxide, potassium hydroxide, sodium carbonate, and potassium carbonate. Specific examples of the basic amino acid include arginine and lysine. Specific examples of the salt include an ammonium salt. Only one kind of alkaline agent may be used, or two or more kinds thereof may be used in combination. When at least one of alkanolamine and ammonia is used as the alkaline agent, the effect of bleaching or destaining of hair by the first hair cosmetic composition is improved.

The alkaline agent is contained in the first agent in such an amount that the pH of the first agent is preferably within a range of 8 to 12. When the pH of the first agent is 8 or higher, the action of the oxidizing agent contained in the second agent is sufficiently promoted upon mixing of the first and second agents. When the pH of the first agent is 12 or lower, hair is less likely to be damaged by the first hair cosmetic composition.

The first agent may contain a component other than the aforementioned components, for example, water, a water-soluble polymer compound, an oil component, an additional polyhydric alcohol, a surfactant, sugar, a preservative, a stabilizing agent, a pH adjuster, a plant extract, a crude drug extract, a vitamin, a fragrance, an anti-oxidant, an ultraviolet ray-absorber, a chelating agent, and an oxidizing aid, as needed.

Water acts as, for example, a solvent.

As the water-soluble polymer compound, any of anionic, cationic, nonionic, and amphoteric ones may be used and any of natural compounds and synthetic compounds may be used. For example, hydroxyethyl cellulose, which is a nonionic synthetic polymer compound, may be used.

The oil component acts to moisturize hair. Specific examples of the oil component include oil/fat, wax, a higher alcohol, a hydrocarbon, a higher fatty acid, an alkylglyceryl ether, an ester, and silicone.

Specific examples of the oil/fat include lanolin, olive oil, camellia oil, shea butter, almond oil, safflower oil, sunflower oil, soybean oil, cottonseed oil, sesame oil, corn oil, rapeseed oil, rice bran oil, rice germ oil, grape seed oil, avocado oil, macadamia nut oil, castor oil, coconut oil, and evening primrose oil. Specific examples of the wax include beeswax, candelilla wax, carnauba wax, jojoba oil, and lanolin. Specific examples of the higher alcohol include cetyl alcohol (cetanol), 2-hexyldecanol, stearyl alcohol, isostearyl alcohol, cetostearyl alcohol, oleyl alcohol, arachyl alcohol, behenyl alcohol, 2-octyldodecanol, lauryl alcohol, myristyl alcohol, decyltetradecanol, and lanolin alcohol.

Specific examples of the hydrocarbon include paraffin, an olefin oligomer, polyisobutene, hydrogenated polyisobutene, mineral oil, squalane, polybutene, polyethylene, microcrystalline wax, and petrolatum. Specific examples of the higher fatty acid include lauric acid, myristic acid, palmitic acid, stearic acid, behenic acid, isostearic acid, 12-hydroxystearic acid, oleic acid, and a lanolin fatty acid. Specific examples of the alkylglyceryl ether include batyl alcohol, chimyl alcohol, serachyl alcohol, and isostearyl glyceryl ether.

Specific examples of the ester include diisopropyl adipate, isopropyl myristate, cetyl octanoate, isononyl isononanoate, octyldodecyl myristate, isopropyl palmitate, stearyl stearate, myristyl myristate, isotridecyl myristate, 2-ethylhexyl palmitate, octyldodecyl ricinoleate, a cholesteryl/lanosteryl fatty acid having a carbon number of 10 to 30, cetyl lactate, acetylated lanolin, ethylene glycol di-2-ethylhexanoate, a pentaerythritol fatty acid ester, a dipentaerythritol fatty acid ester, cetyl caprate, glyceryl tricaprate, diisostearyl malate, dioctyl succinate, and cetyl 2-ethylhexanoate.

Specific examples of the silicone include dimethylpolysiloxane (dimethicone), methylphenylpolysiloxane, decamethylcyclopentasiloxane, dodecamethylcyclohexasiloxane, terminal hydroxyl group-modified dimethylpolysiloxane, polyether-modified silicone, amino-modified silicone, betaine-modified silicone, alkyl-modified silicone, alkoxy-modified silicone, mercapto-modified silicone, carboxyl-modified silicone, and fluorine-modified silicone.

Only one kind of oil component may be used, or two or more kinds thereof may be used in combination.

Specific examples of the polyhydric alcohol include a glycol compound and a glycerin compound. Specific examples of the glycol compound include ethylene glycol, diethylene glycol, triethylene glycol, polyethylene glycol having a number average molecular weight of less than 10,000, propylene glycol, dipropylene glycol, and isoprene glycol. Specific examples of the glycerin compound include glycerin and polyglycerin other than diglycerin.

The surfactant acts as an emulsifying agent or a solubilizing agent, and is used for adjusting the viscosity or improving the viscosity stability. As the surfactant, any of anionic, cationic, amphoteric, and nonionic surfactants may be used.

Specific examples of the anionic surfactant include alkyl ether sulfate, alkyl sulfate, alkenyl ether sulfate, alkenyl sulfate, olefin sulfonate, alkanesulfonate, a saturated or unsaturated fatty acid salt, alkyl or alkenyl ether carbonate, an α-sulfofatty acid salt, an N-acylamino acid type surfactant, a phosphate mono- or di-ester type surfactant, and a sulfosuccinate ester. A counterion for the anionic group of these surfactants may be, for example, any of a sodium ion, a potassium ion, and triethanolamine. For example, sodium lauryl sulfate, which is alkyl sulfate, may be used as the surfactant.

Specific examples of the cationic surfactant include lauryltrimethylammonium chloride, cetyltrimethylammonium chloride, stearyltrimethylammonium chloride, alkyltrimethylammonium chloride, distearyldimethylammonium chloride, cetyltrimethylammonium bromide, stearyltrimethylammonium bromide, lanolin fatty acid aminopropylethyldimethylammonium ethyl sulfate, stearyltrimethylammonium saccharin, cetyltrimethylammonium saccharin, methacryloyloxyethyltrimethylammonium chloride, and behenyltrimethylammonium methyl sulfate.

Specific examples of the amphoteric surfactant include cocobetaine, lauramidopropyl betaine, cocamidopropyl betaine, sodium lauroamphoacetate, sodium cocoamphoacetate, and laurylbetaine (betaine lauryldimethylamino acetate).

Specific examples of the nonionic surfactant include an ether-type nonionic surfactant and an ester-type nonionic surfactant.

Specific examples of the ether-type nonionic surfactant include polyoxyethylene (hereinafter, referred to as POE) cetyl ether (Ceteth), POE stearyl ether (Steareth), POE behenyl ether, POE oleyl ether (Oleth), POE lauryl ether (Laureth), POE octyldodecyl ether, POE hexyldecyl ether, POE isostearyl ether, POE nonylphenyl ether, and POE octylphenyl ether.

Specific examples of the ester-type nonionic surfactant include POE sorbitan monooleate, POE sorbitan monostearate, POE sorbitan monopalmitate, POE sorbitan monolaurate, POE sorbitan trioleate, POE glyceryl monostearate, POE glyceryl monomyristate, POE sorbitol tetraoleate, POE sorbitol hexastearate, POE sorbitol monolaurate, POE sorbitol beeswax, polyethylene glycol monooleate, polyethylene glycol monostearate, polyethylene glycol monolaurate, lipophilic glyceryl monooleate, lipophilic glyceryl monostearate, self-emulsifying glyceryl monostearate, sorbitan monooleate, sorbitan sesquioleate, sorbitan trioleate, sorbitan monostearate, sorbitan monopalmitate, sorbitan monolaurate, a sucrose fatty acid ester, decaglyceryl monolaurate, decaglyceryl monostearate, decaglyceryl monooleate, and decaglyceryl monomyristate.

Only one kind of surfactant may be used, or two or more kinds thereof may be used in combination.

Specific examples of the sugar include sorbitol and maltose.

Specific examples of the preservative include paraben.

Specific examples of the stabilizer include phenacetin, 8-hydroxyquinoline, acetanilide, sodium pyrophosphate, barbituric acid, uric acid, and tannic acid.

Specific examples of the pH adjuster include lactic acid, levulinic acid, glycolic acid, tartaric acid, malic acid, pyrrolidone carboxylic acid (PCA), succinic acid, citric acid, glutamic acid, and arginine.

Specific examples of the antioxidant include ascorbic acid and sulfite.

Specific examples of the chelating agent include ethylenediaminetetraacetic acid (EDTA), diethylenetriaminepentaacetic acid and salts thereof, and hydroxyethanediphosphonic acid (HEDP) and salts thereof.

Specific examples of the oxidizing aid include persulfate such as ammonium persulfate, potassium persulfate, and sodium persulfate. An oxidizing aid is used to intensify bleaching or destaining of hair by the first hair cosmetic composition.

No particular limitation is imposed on the form of the first agent, and the first agent can be in the form of, for example, any of solid, liquid, gel, foam, and cream. Specific examples of the solid form include powder and a granule. Specific examples of the liquid form include an aqueous solution, a suspension, and an emulsified liquid. When the first agent is in the form of solid, the first agent may further contain a dispersant. Specific examples of the dispersant include a metallic salt of stearic acid such as calcium stearate and magnesium stearate, talc, crystalline cellulose, low-substituted hydroxypropyl cellulose, dextrin, and starch.

(Second Agent of First Hair Cosmetic Composition)

An oxidizing agent contained in the second agent acts to remove melanin from hair. Examples of the oxidizing agent used include hydrogen peroxide, urea peroxide, melamine peroxide, sodium percarbonate, potassium percarbonate, sodium perborate, potassium perborate, ammonium persulfate, sodium peroxide, potassium peroxide, magnesium peroxide, barium peroxide, calcium peroxide, strontium peroxide, a hydrogen peroxide adduct of sulfate, a hydrogen peroxide adduct of phosphate, and a hydrogen peroxide adduct of pyrophosphate.

The content of an oxidizing agent in the second agent is preferably 0.1 to 15.0% by mass, more preferably 2.0 to 9.0% by mass, and further preferably 3.0 to 6.0% by mass. When the oxidizing agent content is 0.1% by mass or more, melanin in hair is sufficiently removed. When the oxidizing agent content is 15.0% by mass or less, hair is less likely to be damaged by the first hair cosmetic composition.

When the second agent contains hydrogen peroxide as the oxidizing agent, a stabilizer improving the stability of hydrogen peroxide, for example, ethyleneglycol phenyl ether (phenoxyethanol), hydroxyethanediphosphonic acid, or a salt thereof is preferably added to the second agent. Specific examples of the hydroxyethanediphosphonate include tetrasodium hydroxyethanediphosphonate and disodium hydroxyethanediphosphonate.

The second agent may further contain a component that is generally contained in a composition used for bleaching or destaining hair as long as it does not block the action of each component of the second agent. For example, the second agent may contain a component that is contained in the aforementioned first agent but other than the alkaline agent.

No particular limitation is imposed on the form of the second agent, and the second agent can be in the form of, for example, any of solid (except for the case in which the oxidizing agent is liquid at a normal temperature), liquid, gel, foam, and cream. Specific examples of the solid form include powder and a granule. Specific examples of the liquid form include an emulsified liquid.

The first and second agents are used for bleaching or destaining hair by mixing both of the agents upon application and applying the necessary amount of the resulting mixture to hair using a comb or a brush.

(Second Hair Cosmetic Composition)

The second hair cosmetic composition is a three-part type composed of a first, a second, and a third agent, which are mixed upon application, used for bleaching or destaining hair.

The first agent of the second hair cosmetic composition has a formulation similar to that of the first agent of the first hair cosmetic composition except that it does not contain diglycerin, 1,3-butylene glycol, and polyethylene glycol, and contains at least an alkaline agent.

The second agent of the second hair cosmetic composition has the same formulation as the second agent of the first hair cosmetic composition, and contains at least an oxidizing agent.

The third agent of the second hair cosmetic composition has the same formulation as the first agent of the first hair cosmetic composition, and is in the form of powder or cream.

(Third Hair Cosmetic Composition)

The third hair cosmetic composition is a one-part type used for bleaching hair. The third hair cosmetic composition is contained in a container, for example an applicator container, and upon application, the composition is ejected from the container and applied to hair. The third hair cosmetic composition contains diglycerin, 1,3-butylene glycol, and polyethylene glycol having a number average molecular weight of 10,000 or more, and preferably further contains an alkaline agent and an oxidizing agent. The third hair cosmetic composition is in the form of powder; therefore, the alkaline agent and the oxidizing agent used are preferably in the form of powder. The third hair cosmetic composition may further contain a component that is generally contained in a composition used for bleaching hair as long as it does not block the action of each component of the third hair cosmetic composition.

According to the first embodiment, the following advantages can be attained.

Diglycerin, 1,3-butylene glycol, and polyethylene glycol contained in the first, second, and third hair cosmetic compositions act to improve the ease of application of the hair cosmetic compositions to hair. More specifically, these components delay drying of each of hair cosmetic composition applied on hair, whereby preventing the viscosity of the hair cosmetic composition applied on hair from increasing with time. Thus, even when hair is combed after a certain time after application of each of the hair cosmetic composition to hair, it is easy to spread the hair cosmetic composition over the entire hair. Hence, by using any of the first, second, and third hair cosmetic compositions, hair can be evenly bleached or destained.

When the number average molecular weight of polyethylene glycol contained in each of the first, second, and third hair cosmetic compositions is 20,000 or more, the uniformity of bleaching or destaining of hair by the hair cosmetic composition is improved.

The first embodiment may be modified as follows.

Diglycerin, 1,3-butylene glycol, and polyethylene glycol may be contained in any of the agents that make up a multi-part type hair cosmetic composition. For example, although diglycerin, 1,3-butylene glycol, and polyethylene glycol are contained in the first agent of the first hair cosmetic composition, at least some of these components may be contained in the second agent of the first hair cosmetic composition, instead of the first agent. Also, although diglycerin, 1,3-butylene glycol, and polyethylene glycol are contained in the third agent of the second hair cosmetic composition, at least some of these components may be contained in the first or the second agent of the second hair cosmetic composition, instead of the third agent.

Each of the first, second, and third hair cosmetic compositions may be modified to a multi-part type composed of four or more agents.

Second Embodiment

Hereinbelow, a second embodiment, in which the present invention is embodied as a fourth hair cosmetic composition used for dyeing hair, will be described. The fourth hair cosmetic composition is a two-part type composed of a first and a second agent, which are mixed upon application.

The first agent of the fourth hair cosmetic agent contains diglycerin, 1,3-butylene glycol, polyethylene glycol having a number average molecular weight of 10,000 or more, an alkaline agent, and an oxidation dye. The second agent of the fourth hair cosmetic composition has the same formulation as the second agent of the first hair cosmetic composition, and contains at least an oxidizing agent.

The oxidation dye contained in the first agent can produce color as induced by oxidative polymerization by the oxidizing agent contained in the second agent. The oxidation dye contains at least a dye intermediate, and may additionally contain a coupler.

Specific examples of the dye intermediate include p-phenylenediamine, toluene-2,5-diamine (paratoluylenediamine), N-phenyl-p-phenylenediamine, 4,4'-diaminodiphenylamine, p-aminophenol, o-aminophenol, p-methylaminophenol, N,N-bis(2-hydroxyethyl)-p-phenylenediamine, 2-hydroxyethyl-p-phenylenediamine, o-chlor-p-phenylenediamine, 4-amino-m-cresol, 2-amino-4-hydroxyethylamino anisole, 2,4-diaminophenol, and a salt of these substances. Only one kind of dye intermediate may be used, or two or more kinds thereof may be used in combination.

The coupler produces color by binding to the dye intermediate. Specific examples of the coupler include resorcine, 5-amino-o-cresol, m-aminophenol, α-naphthol, 5-(2-hydroxyethylamino)-2-methylphenol, m-phenylenediamine, 2,4-diaminophenoxyethanol, toluene-3,4-diamine, 2,6-diaminopyridine, diphenylamine, N,N-diethyl-m-aminophenol, phenylmethylpyrazolone, and a salt of these substances. Only one kind of coupler may be used, or two or more kinds thereof may be used in combination. An oxidation dye containing a dye intermediate and a coupler is preferably used since the dye is capable of changing the color tone of hair as desired.

The first agent of the fourth hair cosmetic composition may further contain, for example, at least one selected from oxidation dyes listed in "the Japanese Standards of Quasi-drug Ingredients" (published in June 2006, Yakuji Nippo Ltd.) and direct dyes.

No particular limitation is imposed on the form of the first and second agents, and they can be in the form of, for example, any of solid, liquid, gel, foam, and cream. Specific examples of the liquid form include an aqueous solution, a suspension, and an emulsified liquid. The first and second agents are used for dyeing hair by mixing both of the agents upon application and applying the necessary amount of the resulting mixture to hair using a comb or a brush.

According to the second embodiment, the following advantages can be attained.

Diglycerin, 1,3-butylene glycol, and polyethylene glycol contained in the fourth hair cosmetic composition act to improve the ease of application of the fourth hair cosmetic composition to hair. More specifically, these components delay drying of the fourth hair cosmetic composition applied on hair, whereby preventing the viscosity of the fourth hair cosmetic composition applied on hair from increasing with time. Thus, even when hair is combed after a certain time after application of the fourth hair cosmetic composition to hair, the fourth hair cosmetic composition is spread over the entire hair easily. Hence, by using the fourth hair cosmetic composition, hair can be evenly dyed.

When the number average molecular weight of polyethylene glycol contained in the fourth hair cosmetic composition is 20,000 or more, or more specifically, 30,000 or more, the uniformity of dyeing of hair by the hair cosmetic composition is improved.

The second embodiment may be modified as follows.

The fourth hair cosmetic composition may be modified to a three-part type similar to the second hair cosmetic composition or a one-part type similar to the third hair cosmetic composition. Alternatively, the fourth hair cosmetic composition may be modified to a multi-part type composed of four or more agents.

Examples

Subsequently, the present invention will be further specifically described with Examples and Comparative Examples.

The hair dyes (hair cosmetic compositions) of Examples 1 to 17 and Comparative Examples 1 to 8 were prepared. Each of the hair dyes is a two-part type, in which the first agent has the formulation as shown in Table 1 or 2, and the second agent has a common formulation as shown in Table 3. The unit of the content of each component of a hair dye as shown in Tables 1 to 3 is % by mass. The first and second agents of each of the hair dyes were mixed at a mass ratio of 1:1, and the resulting mixture was applied to a bundle of black human hair using a brush. The hair bundle was left at room temperature (25° C.) for 30 minutes, and then the hair dye adhering to the hair bundle was washed off with water. Furthermore, the hair bundle was shampooed twice and conditioned once. The hair bundle was blow-dried with warm air, and then left for a day. At this time, ease of combing, ease of application, and level-dyeing properties were evaluated according to the method described below.

(Evaluation Method for Ease of Combing)

Twenty panelists were asked to comb the hair bundle 10 minutes after application of each of the hair dyes. The hair dye was rated as "5", "4", "3", "2", "1", or "0" when the number of panelists who responded that the hair dye applied on hair bundle had not dried yet and the hair bundle was smoothly combed was 17 or more, 13 to 16, 9 to 12, 5 to 8, 2 to 4, and 0 to 1, out of 20, respectively. The results of evaluation are shown in Tables 1 and 2.

(Evaluation Method for Ease of Application)

Twenty panelists were asked to apply each of the hair dyes to the hair bundle. The hair dye was rated as "5", "4", "3", "2", "1", or "0" when the number of panelists who responded that the hair dye was easily applied with good spreadability was 17 or more, 13 to 16, 9 to 12, 5 to 8, 2 to 4, and 0 to 1, out of 20, respectively. The results of evaluation are shown in Tables 1 and 2.

(Evaluation Method for Level-Dyeing Properties)

Ten panelists were asked to visually observe the hair bundle dyed with each of the hair dyes under a standard light source, and score the uniformity of color tone of hair bundle on a 5-point scale, namely excellent (5 points), good (4 points), fair (3 points), slightly poor (2 points), and poor (1 point). The hair dye was rated as "excellent (5 points)", "good (4 points)", "fair (3 points)", "slightly poor (2 points)", or "poor (1 point)" when the average score was 4.6 or more, 3.6 or more and less than 4.6, 2.6 or more and less than 3.6, 1.6 or more and less than 2.6, and less than 1.6, respectively. The results of evaluation are shown in Tables 1 and 2.

TABLE 1

| Mixed components | Examples | | | | | | Comparative Examples | | | | | | | |
|---|---|---|---|---|---|---|---|---|---|---|---|---|---|---|
| | 1 | 2 | 3 | 4 | 5 | 6 | 1 | 2 | 3 | 4 | 5 | 6 | 7 | 8 |
| Diglycerin | 1 | 1 | 1 | 1 | 1 | 1 | — | — | — | 6 | 1 | 1 | 1 | 1 |
| Dipropylene glycol | — | — | — | — | — | — | — | — | 1 | — | — | — | — | — |
| 1,3-Butylene glycol | 5 | 5 | 5 | 5 | 5 | 5 | 6 | 5 | 5 | — | — | 5 | 5 | — |
| Propylene glycol | — | — | — | — | — | — | — | — | — | — | 5 | — | — | 5 |
| Polyethylene glycol 10000 (molecular weight: 10,000) | 0.1 | — | — | — | — | — | — | — | — | — | — | — | — | — |
| Polyethylene glycol 20000 (molecular weight: 20,000) | — | 0.1 | — | — | — | — | — | — | — | — | — | — | — | — |
| Polyethylene glycol 35000 (molecular weight: 35,000) | — | — | 0.1 | — | — | — | — | — | — | — | — | — | — | — |
| Polyethylene glycol PEG-9M (molecular weight: 400,000) | — | — | — | 0.1 | 0.1 | — | — | — | — | — | — | — | — | — |
| Polyethylene glycol PEG-90M (molecular weight: 4,000,000) | — | — | — | — | — | 0.1 | 0.1 | 0.1 | 0.1 | 0.1 | 0.1 | — | — | — |
| Polyethylene glycol 6000 (molecular weight: 6,000) | — | — | — | — | 0.1 | — | — | — | — | — | — | — | 0.1 | — |
| Polypropylene glycol 4000 (molecular weight: 4,000) | — | — | — | — | — | — | — | — | — | — | — | — | — | 0.1 |

TABLE 1-continued

| Mixed components | Examples | | | | | | Comparative Examples | | | | | | | |
|---|---|---|---|---|---|---|---|---|---|---|---|---|---|---|
| | 1 | 2 | 3 | 4 | 5 | 6 | 1 | 2 | 3 | 4 | 5 | 6 | 7 | 8 |
| Cetostearyl alcohol | 6 | 6 | 6 | 6 | 6 | 6 | 6 | 6 | 6 | 6 | 6 | 6 | 6 | 6 |
| POE(7)Cetyl ether | 2 | 2 | 2 | 2 | 2 | 2 | 2 | 2 | 2 | 2 | 2 | 2 | 2 | 2 |
| POE(10)Cetyl ether | 4 | 4 | 4 | 4 | 4 | 4 | 4 | 4 | 4 | 4 | 4 | 4 | 4 | 4 |
| POE(20)Cetyl ether | 3 | 3 | 3 | 3 | 3 | 3 | 3 | 3 | 3 | 3 | 3 | 3 | 3 | 3 |
| Stearyl-trimethyl-ammonium chloride | 0.3 | 0.3 | 0.3 | 0.3 | 0.3 | 0.3 | 0.3 | 0.3 | 0.3 | 0.3 | 0.3 | 0.3 | 0.3 | 0.3 |
| Hydroxyethyl cellulose | 0.3 | 0.3 | 0.3 | 0.3 | 0.3 | 0.3 | 0.3 | 0.3 | 0.3 | 0.3 | 0.3 | 0.3 | 0.3 | 0.3 |
| Glycerin | 2 | 2 | 2 | 2 | 2 | 2 | 2 | 4 | 2 | 2 | 2 | 2 | 2 | 2 |
| Light liquid isoparaffin | 2 | 2 | 2 | 2 | 2 | 2 | 2 | 2 | 2 | 2 | 2 | 2 | 2 | 2 |
| Sodium sulfite | 0.1 | 0.1 | 0.1 | 0.1 | 0.1 | 0.1 | 0.1 | 0.1 | 0.1 | 0.1 | 0.1 | 0.1 | 0.1 | 0.1 |
| Hydroxy-ethanedi-phosphonic acid | 0.1 | 0.1 | 0.1 | 0.1 | 0.1 | 0.1 | 0.1 | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 | 0.3 | 0.3 | 0.3 | 0.3 | 0.3 | 0.3 | 0.3 |
| p-Phenyl-enediamine | 0.4 | 0.4 | 0.4 | 0.4 | 0.4 | 0.4 | 0.4 | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 | 0.15 | 0.15 | 0.15 | 0.15 | 0.15 | 0.15 | 0.15 |
| 2,4-Diamino-phenoxy-ethanol | 0.05 | 0.05 | 0.05 | 0.05 | 0.05 | 0.05 | 0.05 | 0.05 | 0.05 | 0.05 | 0.05 | 0.05 | 0.05 | 0.05 |
| 28% Ammonia water | 5 | 5 | 5 | 5 | 5 | 5 | 5 | 5 | 5 | 5 | 5 | 5 | 5 | 5 |
| Mono-ethanolamine | 1 | 1 | 1 | 1 | 1 | 1 | 1 | 1 | 1 | 1 | 1 | 1 | 1 | 1 |
| Purified water | Balance | Balance | Balance | Balance | Balance | Balance | Balance | Balance | Balance | Balance | Balance | Balance | Balance | Balance |
| Total | 100 | 100 | 100 | 100 | 100 | 100 | 100 | 100 | 100 | 100 | 100 | 100 | 100 | 100 |
| Evaluation | | | | | | | | | | | | | | |
| Ease of combing | 5 | 5 | 5 | 5 | 5 | 5 | 2 | 2 | 2 | 2 | 2 | 2 | 3 | 2 |
| Ease of application | 4 | 5 | 5 | 5 | 5 | 5 | 3 | 3 | 3 | 3 | 3 | 1 | 1 | 1 |
| Level-dyeing properties | 3 | 5 | 5 | 5 | 5 | 5 | 2 | 2 | 2 | 2 | 2 | 1 | 1 | 1 |

TABLE 2

| Mixed components | Examples | | | | | | | | | | |
|---|---|---|---|---|---|---|---|---|---|---|---|
| | 7 | 8 | 9 | 10 | 11 | 12 | 13 | 14 | 15 | 16 | 17 |
| Diglycerin | 0.1 | 5 | 10 | 1 | 1 | 1 | 1 | 1 | 1 | 1 | 1 |
| 1,3-Butylene glycol | 5 | 5 | 5 | 0.5 | 2 | 10 | 15 | 5 | 5 | 5 | 5 |
| Polyethylene glycol PEG-90M (molecular weight: 4,000,000) | 0.1 | 0.1 | 0.1 | 0.1 | 0.1 | 0.1 | 0.1 | 0.005 | 0.01 | 2 | 5 |
| Cetostearyl alcohol | 6 | 6 | 6 | 6 | 6 | 6 | 6 | 6 | 6 | 6 | 6 |
| POE(7)Cetyl ether | 2 | 2 | 2 | 2 | 2 | 2 | 2 | 2 | 2 | 2 | 2 |
| POE(10)Cetyl ether | 4 | 4 | 4 | 4 | 4 | 4 | 4 | 4 | 4 | 4 | 4 |
| POE(20)Cetyl ether | 3 | 3 | 3 | 3 | 3 | 3 | 3 | 3 | 3 | 3 | 3 |
| Stearyltrimethylammonium chloride | 0.3 | 0.3 | 0.3 | 0.3 | 0.3 | 0.3 | 0.3 | 0.3 | 0.3 | 0.3 | 0.3 |
| Hydroxyethyl cellulose | 0.3 | 0.3 | 0.3 | 0.3 | 0.3 | 0.3 | 0.3 | 0.3 | 0.3 | 0.3 | 0.3 |
| Glycerin | 2 | 2 | 2 | 2 | 2 | 2 | 2 | 2 | 2 | 2 | 2 |

TABLE 2-continued

| Mixed components | Examples | | | | | | | | | | |
|---|---|---|---|---|---|---|---|---|---|---|---|
| | 7 | 8 | 9 | 10 | 11 | 12 | 13 | 14 | 15 | 16 | 17 |
| Light liquid isoparaffin | 2 | 2 | 2 | 2 | 2 | 2 | 2 | 2 | 2 | 2 | 2 |
| Sodium sulfite | 0.1 | 0.1 | 0.1 | 0.1 | 0.1 | 0.1 | 0.1 | 0.1 | 0.1 | 0.1 | 0.1 |
| Hydroxyethanediphosphonic acid | 0.1 | 0.1 | 0.1 | 0.1 | 0.1 | 0.1 | 0.1 | 0.1 | 0.1 | 0.1 | 0.1 |
| Fragrance | 0.1 | 0.1 | 0.1 | 0.1 | 0.1 | 0.1 | 0.1 | 0.1 | 0.1 | 0.1 | 0.1 |
| L-Ascorbic acid | 0.3 | 0.3 | 0.3 | 0.3 | 0.3 | 0.3 | 0.3 | 0.3 | 0.3 | 0.3 | 0.3 |
| p-Phenylenediamine | 0.4 | 0.4 | 0.4 | 0.4 | 0.4 | 0.4 | 0.4 | 0.4 | 0.4 | 0.4 | 0.4 |
| p-Aminophenol | 0.6 | 0.6 | 0.6 | 0.6 | 0.6 | 0.6 | 0.6 | 0.6 | 0.6 | 0.6 | 0.6 |
| m-Aminophenol | 0.15 | 0.15 | 0.15 | 0.15 | 0.15 | 0.15 | 0.15 | 0.15 | 0.15 | 0.15 | 0.15 |
| 5-Amino-orthocresol | 0.15 | 0.15 | 0.15 | 0.15 | 0.15 | 0.15 | 0.15 | 0.15 | 0.15 | 0.15 | 0.15 |
| 2,4-Diaminophenoxyethanol | 0.05 | 0.05 | 0.05 | 0.05 | 0.05 | 0.05 | 0.05 | 0.05 | 0.05 | 0.05 | 0.05 |
| 28% Ammonia water | 5 | 5 | 5 | 5 | 5 | 5 | 5 | 5 | 5 | 5 | 5 |
| Monoethanolamine | 1 | 1 | 1 | 1 | 1 | 1 | 1 | 1 | 1 | 1 | 1 |
| Purified water | Balance | Balance | Balance | Balance | Balance | Balance | Balance | Balance | Balance | Balance | Balance |
| Total | 100 | 100 | 100 | 100 | 100 | 100 | 100 | 100 | 100 | 100 | 100 |
| Evaluation | | | | | | | | | | | |
| Ease of combing | 4 | 5 | 5 | 3 | 4 | 5 | 5 | 5 | 5 | 5 | 5 |
| Ease of application | 4 | 5 | 4 | 3 | 5 | 5 | 4 | 3 | 4 | 5 | 4 |
| Level-dyeing properties | 4 | 5 | 4 | 3 | 4 | 5 | 4 | 3 | 4 | 5 | 4 |

TABLE 3

<Second agent>

| Components | |
|---|---|
| Cetanol | 3 |
| POE (30) Cetyl ether | 0.6 |
| POE (5,5) Cetyl ether | 0.2 |
| 35% Hydrogen peroxide water | 16.6 |
| Purified water | Balance |
| Total | 100 |

As shown in Tables 1 and 2, the hair dyes of Examples 1 to 17 were rated as "3" or higher in any of the evaluation items of ease of combing, ease of application, and level-dyeing properties.

In contrast, the ease of combing and the level-dyeing properties of the hair dye of Comparative Example 1 lacking diglycerin, the hair dye of Comparative Example 2 containing additional glycerin instead of diglycerin, and the hair dye of Comparative Example 3 containing dipropylene glycol instead of diglycerin were evaluated lower than those of the hair dyes of Examples.

The ease of combing and the level-dyeing properties of the hair dye of Comparative Example 4 lacking 1,3-butylene glycol and the hair dye of Comparative Example 5 containing propylene glycol instead of 1,3-butylene glycol were evaluated lower than those of the hair dyes of Examples.

The ease of application and the level-dyeing properties of the hair dye of Comparative Example 6 lacking polyethylene glycol and the hair dye of Comparative Example 7 containing polyethylene glycol having a molecular weight of 6,000 were evaluated lower than those of the hair dyes of Examples.

The ease of application and the level-dyeing properties of the hair dye of Comparative Example 8 containing propylene glycol instead of 1,3-butylene glycol and also polyethylene glycol having a molecular weight of 4000 were evaluated lower than those of the hair dyes of Examples.

The invention claimed is:

1. A hair cosmetic composition used for dyeing, bleaching, or destaining hair, comprising diglycerin, 1,3-butylene glycol, and polyethylene glycol having a number average molecular weight of 10,000 or more.

2. The hair cosmetic composition according to claim 1, wherein the number average molecular weight of the polyethylene glycol is 20,000 or more.

3. The hair cosmetic composition according to claim 1, comprising 0.005 to 10% by mass of the diglycerin, 0.05 to 15% by mass of the 1,3-butylene glycol, and 0.0005 to 5% by mass of the polyethylene glycol.

* * * * *